(12) United States Patent
Furitsu et al.

(10) Patent No.: US 6,743,443 B1
(45) Date of Patent: Jun. 1, 2004

(54) TABLETS IMMEDIATELY DISINTEGRATING IN THE ORAL CAVITY

(75) Inventors: Hisao Furitsu, Ibaraki (JP); Akira Kato, Ibaraki (JP); Takayuki Ohwaki, Aichi (JP); Masanobu Yasui, Saitama (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/806,823

(22) PCT Filed: Sep. 28, 1999

(86) PCT No.: PCT/JP99/05298

§ 371 (c)(1),
(2), (4) Date: Apr. 5, 2001

(87) PCT Pub. No.: WO00/20033

PCT Pub. Date: Apr. 13, 2000

(30) Foreign Application Priority Data

Oct. 5, 1998 (JP) ............................................. 10-282378
Oct. 19, 1998 (JP) ............................................. 10-295947

(51) Int. Cl.$^7$ ............................ A61K 9/20; A61K 9/28
(52) U.S. Cl. ...................... 424/465; 424/435; 424/441; 424/464; 424/474
(58) Field of Search ................................ 424/464, 465, 424/441

(56) References Cited

U.S. PATENT DOCUMENTS

| | | |
|---|---|---|
| 4,610,875 A | 9/1986 | Panoz et al. |
| 4,892,741 A | 1/1990 | Ohm et al. ................... 424/479 |
| 5,264,446 A | 11/1993 | Hegasy et al. |
| 5,466,464 A | 11/1995 | Masaki et al. |
| 5,998,437 A | 12/1999 | Nishi et al. |
| 6,403,597 B1 * | 6/2002 | Wilson et al. ............... 514/256 |
| 2002/0002172 A1 * | 1/2002 | Bell-Huff et al. ............ 514/258 |
| 2002/0004498 A1 * | 1/2002 | Doherty, Jr. et al. ......... 514/182 |
| 2003/0004170 A1 * | 1/2003 | Podolski ................. 514/252.16 |

FOREIGN PATENT DOCUMENTS

| | | |
|---|---|---|
| EP | 0521310 A2 | 1/1993 |
| EP | A2521310 | 1/1993 |

(List continued on next page.)

OTHER PUBLICATIONS

M. Boolell et al., British Journal of Urology, 78, pp. 257–261 (1996).

Primary Examiner—James M. Spear
(74) Attorney, Agent, or Firm—Birch, Stewart, Kolasch & Birch, LLP (57) ABSTRACT

The present invention provides an intraoral quickly disintegrating tablet containing a phosphodiesterase inhibitor having an effect of improving the erectile dysfunction and a method for manufacturing the tablet. The present invention also provides an intraoral quickly disintegrating tablet containing a slightly soluble pharmaceutical agent having an improved solubility and a method for manufacturing the tablet. That is, it is an intraoral quickly disintegrating tablet containing a cyclic GMP phosphodiesterase inhibitor and a saccharide, and a method for manufacturing the tablet. Further, it is a method for manufacturing an intraoral quickly disintegrating tablet, which comprises dissolving a slightly soluble pharmaceutical agent in an organic solvent or an aqueous organic solvent together with a surfactant and/or a water-soluble polymer, coating the solution on a filler or granulating it with a filler to obtain molded products, mixing a saccharide with them, adding an organic solvent, water or an aqueous organic solvent thereto, followed by kneading, and subjecting it to a compression-molding.

7 Claims, 2 Drawing Sheets

●: intraoral quickly disintegrating tablet
○: the pharmaceutical ingredient per se

FOREIGN PATENT DOCUMENTS

| | | |
|---|---|---|
| EP | 0636626 A1 | 2/1995 |
| EP | A1636626 | 2/1995 |
| EP | A1779887 | 6/1997 |
| EP | 0807433 A1 | 11/1997 |
| EP | A1807433 | 11/1997 |
| JP | A5622725 | 3/1981 |
| JP | 56022725 A | 3/1981 |
| JP | 58183615 | 10/1983 |
| JP | 5914446 | 4/1984 |
| JP | 05271054 | 10/1993 |
| JP | 06218028 A | 8/1994 |
| JP | 770128 | 3/1995 |
| JP | 0819589 A | 1/1996 |
| JP | 08310969 A | 11/1996 |
| JP | A8310969 | 11/1996 |
| JP | 0948726 A | 2/1997 |
| JP | 9503996 | 4/1997 |
| JP | 10114657 A | 5/1998 |
| JP | A10167966 | 6/1998 |
| JP | 10167966 A | 6/1998 |
| JP | 2807346 | 7/1998 |
| WO | A1937124 | 4/1993 |
| WO | 9307124 | 4/1993 |
| WO | 9319742 | 10/1993 |
| WO | A1-9319742 | 10/1993 |
| WO | 9428902 | 12/1994 |
| WO | 9703070 | 1/1997 |
| WO | A1973675 | 2/1997 |
| WO | 9703675 | 2/1997 |
| WO | A1987430 | 2/1998 |
| WO | 9807430 | 2/1998 |

* cited by examiner

Fig. 1

● : intraoral quickly disintegrating tablet

○ : the pharmaceutical ingredient per se

Fig. 2

● : intraoral quickly disintegrating tablet

○ : the pharmaceutical ingredient per se

Fig. 3

● : intraoral quickly disintegrating tablet

○ : the pharmaceutical ingredient per se

Fig. 4

● : intraoral quickly disintegrating tablet

○ : tablet prepared by the conventional method

TABLETS IMMEDIATELY DISINTEGRATING IN THE ORAL CAVITY

This application is the national phase under 35 U.S.C. §371 of PCT International Application No. PCT/JP99/05298 which has an International filing date of Sep. 28, 1999, which designated the United States of America.

TECHNICAL FIELD

The present invention relates to an intraoral quickly disintegrating tablet containing a phosphodiesterase inhibitor having an effect of improving the erectile dysfunction and to a method for manufacturing the tablet.

The present invention also relates to an intraoral quickly disintegrating tablet containing a slightly soluble pharmaceutical agent such as a phosphodiesterase inhibitor having an improved solubility and to a method for manufacturing the tablet.

PRIOR ART

It is reported in JP-B9-503996 that pyrazonopyrimidinone compounds having an inhibitory action to a cyclic GMP phosphodiesterase type V are useful for the therapy of erectile dysfunction by means of oral administration. Further, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one (general name: sildenafil) belonging to the same classification and being represented by the formula (I) surely shows duration of its pharmaceutical effect at least for two hours when it is orally administered (*British J. Urology*, 78, 257–261, 1996.) and, therefore, there is a high possibility that they are used for a highly practical drug therapy for erectile dysfunction as a substitute for an injection therapy of papaverine hydrochloride or prostaglandin E1 into corpus cavernosum penis which has been carried out in an urological field. In addition, with regard to a compound having an inhibitory action to a cyclic GMP phosphodiesterase type V, there is disclosed a pyrazolopyrimidinone derivative represented by the formula (II) {1,3-dimethyl-6-(2-propoxy-5-methanesulfonamidophenyl)-1,5-dihydropyrazolo[3,4-d]-pyrimidin-4-one} in JP-A 7-70128 while, in WO 97/03675, there are mentioned a compound represented by the formula (IV) {(6R,12aR)-2,3,6,7,12,12a-hexahydro-2-methyl-6-(3,4-methylenedioxyphenyl)-pyrazino[2', 1':6,1]pyrido[3,4-b]-indol-1,4-dione)} and a compound represented by the formula (V) {(3S,6R,12aR)-2,3,6,7,12,12a-hexahydro-2,3-dimethyl-6-(3,4-methylenedioxyphenyl)-pyrazino[2', 1':6,1]pyrido[3,4-b] indol-1,4-dione}.

Further, in WO 93/07124, there is mentioned a compound represented by the formula (III) {2-(4-carboxypiperidino)-4-(3,4-methylenedioxybenzyl)amino-6-chloroquinazoline}. Furthermore, the compounds of a fused pyridazine type represented by the formula (VI) mentioned in JP-A 10-114657 have an inhibitory action to a cyclic GMP phosphodiesterase type V and are useful as therapeutic agents for erectile dysfunction.

It has been said that the number of the latent patients of erectile dysfunction are about 3,000,000 in Japan and are about 20,000,000 in U. S. A. It has been also reported that, while the number of the patients of erectile dysfunction in U. S. A. are only 2–7% of the male population of younger than 50 years age, the rate increases together with aging and 15% of males of fifties and a little over 30% of males of sixties are suffering from this disease. Most of them are derived from organic disorder and, taking the advent of an aging society in near future into consideration, it may be concluded that oral preparations of cyclic GMP phosphodiesterase inhibitors will play a very big role in improving the quality of life (QOL) of the patients suffering from erectile dysfunction.

However, when the conventional oral preparations containing a cyclic GMP phosphodiesterase inhibitor are administered, there is a possibility that, for example, administration of tablets is difficult or that powdery or granular agent adheres in the mouth or comes into artificial teeth whereby a part of the preparation is dropped out since aged people have a low swallowing ability.

When a consideration is made on the standpoint of the aged people as such, there is a very high demand for "therapeutic preparations for erectile dysfunction which can be easily taken, easily swollen and easily handled" which is able to be "one of the means whereby control of the carnal desire which is the fundamental desire of human being can be embodied". Even in ordinary and healthy adults, therapeutic preparations for erectile dysfunction which can be taken at any place without water greatly contribute to their QOL.

On the other hand, intraoral quickly disintegrating tablets have been known as the tablets which are quickly disintegrated in the mouth and, since they can be easily taken without water, they are recently receiving public attention as a dosage form which is suitable for the people having insufficient swallowing functions such as aged people and small children.

It has been known that the intraoral quickly disintegrating tablets can be prepared, for example, by the use of wet powder. With regard to a method where wet powder is dried without a tableting step whereupon the intraoral quickly disintegrating tablets are prepared, there is disclosed for example in JP-A 5-511543 for "a solid preparation which is quickly disintegrated in the mouth comprising an active ingredient, a saccharide selected from lactose and/or mannitol and agar".

On the other hand, with regard to an intraoral quickly disintegrating tablet prepared by a compression-molding of wet powder filled in a molding machine, there are disclosed, for example, "a method for the manufacture of an intraoral quickly disintegrating tablet where a mixture containing a pharmaceutical ingredient, a saccharide and water which is in an amount of moisturizing the particle surface of the saccharide is made into a tablet" in JP-A 5-271054; "an intraoral quickly disintegrating tablet comprising a pharmaceutical agent, a saccharide, a sugar alcohol and a water-soluble polymer and being prepared by moisturizing and molding" in JP-A 9-48726; and "a wet-process tablet where a pharmaceutical agent is mixed with a saccharide, a filler, etc., kneaded after addition of water and/or organic solvent, filled in a mold and subjected to a compression-molding and a method for manufacturing the same" in JP-A 6-218028. Further, with regard to a method for the molding of an intraoral quickly disintegrating tablet, there is disclosed in JP-A 8-19589 for an invention concerning "a method for the manufacture of a tablet where wet powder is filled in a hole for molding the tablet and at least one side of the wet powder in the hole is made into a shape of a tablet by means of a metal mold for molding with a film for prevention of adhesion and an apparatus for manufacturing the tablet".

However, there has been no report yet for a preparation containing a cyclic GMP phosphodiesterase inhibitor and being able to greatly contribute in such a QOL improvement and for a method of manufacturing such a preparation.

Incidentally, in the case of a slightly soluble pharmaceutical agent, it is not preferred to directly apply the intraoral quickly disintegrating tablet using the above-mentioned known means and the method for manufacturing the tablet. That is because the low solubility of the slightly soluble pharmaceutical agent delays the time for reaching the effective blood level by oral administration and long time is required for achieving the pharmaceutical effect and also because there is a risk that a sufficient pharmaceutical effect is not achieved due to a low bioavailability.

In general, one of the most important factors among various factors affecting the absorption of a pharmaceutical agent via digestive tracts is its solubility and, especially in the case of a slightly soluble pharmaceutical agent, it is quite often that its dissolving rate determines the rate of absorption. Various methods have been known for promoting the solubility of a pharmaceutical agent and they may be roughly classified into the following three. Thus, (1) to increase the surface area of the pharmaceutical particles; (2) to use amorphous or metastable crystals; and (3) to utilize various types of salt or to add a solubilizer. As to the specific means therefor, making the pharmaceutical agent into fine powder, formation of a solvate and adsorption on the surface of a carrier have been known for (1); selection of crystal polymorphism, mixing/pulverization and preparation of a solid dispersion have been known for (2); and preparation of an acidic salt or an alkaline salt, addition of various pH buffers and/or surfactants, etc. have been known for (3) and they are disclosed, for example, in JP-A 59-14446 and JP-A 58-183615.

However, there has been no report yet for an intraoral quickly disintegrating tablet containing a slightly soluble pharmaceutical agent having an improved solubility as such and for a method of manufacturing the tablet. One of the reasons therefor is that it is difficult for satisfying all of the requirements for improving the solubility of the slightly soluble pharmaceutical agent, for a quick disintegration in the mouth and for ensuring a good touch on the tongue upon disintegration. Many of the pharmaceutical ingredients acting as a cyclic GMP phosphodiesterase inhibitor are the compounds having a relatively low solubility and are within a category of the slightly soluble pharmaceutical agents. Especially in the weakly acidic to neutral regions which are the pH of the stomach of the persons of anacidity and the pH ranging from duodenum to small intestine which are the main sites for absorption of the pharmaceutical agent, the solubility significantly lowers. Solubilities at 37 ° C. in the first disintegration test solution (pH 1.2) and the second disintegration test solution (pH 6.8) according to the Japanese Pharmacopoeia are 2.52 mg/ml and 0.11 mg/ml, respectively for sildenafil (citrate); 0.13 mg/ml and 0.0063 mg/ml, respectively, for 4-(3-chloro-4-methoxybenzyl) amino-6-cyano-1-(4-hydroxypiperidino)-phthalazine hydrochloride which is represented by the formula (IX) among the phthalazine compounds of the formula (VI); and 0.028 mg/ml and 0.0012 mg/ml, respectively, for 4-(3-chloro-4-methoxyphenethyl)-amino-6-cyano-1-(4-hydroxypiperidino)phthalazine hydrochloride represented by the formula (X).

It is worried about that the slight solubility of the cyclic GMP phosphodiesterase inhibitor agent as such may result in a delay of the time reaching the effective blood level, a lowering of the bioavailability and an expansion of the dispersion thereof.

Accordingly, in a cyclic GMP phosphodiesterase inhibitor having such a low solubility, it is desired that the solubility of the effective ingredient in the intraoral quickly disintegrating tablet is improved so that the time for reaching the effective blood level is made shorter and that the absorption is improved so that the bioavailability is improved.

DISCLOSURE OF THE INVENTION

With regard to a preparation containing a cyclic GMP phosphodiesterase inhibitor, there has been a brisk demand for the development of an oral preparation which is able to contribute in the QOL of the patients suffering from erectile dysfunction or, in other words, an oral preparation which can be easily taken by aged people and can be taken without water even by adults having a swallowing ability and a method for manufacturing the preparation.

To be more specific, there has been a demand for the development of an intraoral quickly disintegrating tablet containing a cyclic GMP phosphodiesterase inhibitor having quick disintegrating property and solubility in the mouth and also having a strength for retaining its shape during preservation and a method of manufacturing the tablet.

There has been also a demand for the development of an intraoral quickly disintegrating tablet containing a slightly soluble pharmaceutical agent having quick disintegrating property and solubility in the mouth, showing a good touch on the tongue upon disintegration in the mouth and having a strength for retaining its shape during preservation and a method of manufacturing the tablet. Thus, it is expected that the solubility of the pharmaceutical ingredient in the intraoral quickly disintegrating tablet is improved whereby the time for reaching the effective blood level is made short, the time until expressing the pharmaceutical effect is made short and absorption is improved so that the bioavailability is improved.

However, although there are many aged people among the patients suffering from erectile dysfunction and there have been so many demands for an intraoral quickly disintegrating tablet containing a cyclic GMP phosphodiesterase inhibitor and to a method for manufacturing the tablet, such tablet and method have not been developed yet. Such a situation is the same for an intraoral quickly disintegrating tablet containing a slightly soluble pharmaceutical agent with an improved solubility and a method for manufacturing the tablet as well.

Under such circumstances, the present inventors have carried out an intensive study for investigating an intraoral quickly disintegrating tablet with an excellent disintegrating property containing a cyclic GMP phosphodiesterase inhibitor and a saccharide and a method for manufacturing the tablet and also for an intraoral quickly disintegrating tablet with an excellent solubility containing a slightly soluble pharmaceutical agent and a saccharide and a method for manufacturing the tablet. As a result, it has been found that the aimed object can be achieved by the constitutions as mentioned below whereupon the present invention has been accomplished.

The present invention is an intraoral quickly disintegrating tablet containing a cyclic GMP phosphodiesterase inhibitor and a saccharide.

Further, the present invention is an intraoral quickly disintegrating tablet containing a cyclic GMP phosphodiesterase inhibitor, a saccharide and a binder.

Furthermore, the present invention is an intraoral quickly disintegrating tablet where a cyclic GMP phosphodiesterase inhibitor and a saccharide are mixed, kneaded with an organic solvent, water or an aqueous organic solvent and subjected to a compression-molding and also a method for manufacturing the tablet.

Still further, the present invention is an intraoral quickly disintegrating tablet where a cyclic GMP phosphodiesterase inhibitor and a saccharide are mixed, kneaded with an organic solvent, water or an aqueous organic solvent, filled in a mold and subjected to a compression-molding with a film and also a method for manufacturing the tablet.

The cyclic GMP phosphodiesterase inhibitor covers both that which is slightly soluble and that which is not slightly soluble.

The cyclic GMP phosphodiesterase inhibitor of the present invention may be selected from the group consisting of:

5-[2-ethoxy-5-(4-methyl-1-piperazinylsulfonyl)phenyl]-1-methyl-3-n-propyl-1,6-dihydro-7H-pyrazolo[4,3-d]pyrimidin-7-one represented the formula (I)

(I)

1,3-dimethyl-6-(2-propoxy-5-methanesulfonamidophenyl)-1,5-dihydropyrazolo[3,4-d]pyrimidin-4-one represented by the formula (II)

(II)

2-(4-carboxypiperidino)-4-(3,4-methylenedioxybenzyl)amino-6-chloroquinazoline represented by the formula (III)

(III)

(6R,12aR)-2,3,6,7,12,12a-hexahydro-2-methyl-6-(3,4-methylenedioxyphenyl)-pyrazino[2', 1':6,1]pyrido[3,4-b]-indol-1,4-dione represented by the formula (IV)

(IV)

(3S,6R,12aR)-2,3,6,7,12,12a-hexahydro-2,3-dimethyl-6-(3,4-methylenedioxyphenyl)-pyrazino[2', 1':6,1]pyrido[3,4-b]-indol-1,4-dione shown by the formula (V)

(V)

or a pharmacologically acceptable salt thereof.

In addition, the cyclic GMP phosphodiesterase inhibitor may be a compound represented by the following formula (VI) or a pharmacologically acceptable salt thereof

(VI)

wherein in the formula,
the ring C is an unsaturated 5- or 6-membered ring which may have a hetero atom;
n is 0 or an integer of 1–4;
$R^1$ is a halogen atom, an optionally substituted lower alkyl group, an, optionally substituted lower alkoxy group, an optionally substituted cycloalkyl group, nitro group, cyano group, a group represented by the formula —$NR^2R^3$, wherein
in the formula, $R^2$ and $R^3$ are the same as or different from each other and each is hydrogen atom, an optionally substituted lower alkyl group, an acyl group, an optionally substituted arylalkyl group or an optionally substituted heteroarylalkyl group, $R^2$ and $R^3$ may form a ring together with a nitrogen atom bonded thereto, which ring may further have a substituent, a group represented by the formula —O—$R^9$, wherein in the formula, R⁹ is hydrogen atom, an optionally substituted lower alkyl group, an acyl group, an optionally substituted arylalkyl group or an optionally substituted heteroarylalkyl group, a group represented by the formula —S—R¹⁰, wherein in the formula, R¹⁰ is hydrogen atom, an optionally substituted lower alkyl group, an acyl group, an optionally substituted arylalkyl group or an optionally substituted heteroarylalkyl group, a group represented by the formula (VII):

wherein in the formula (VII), R¹¹ is hydrogen atom, a lower alkyl group or amino group; and m is 0 or an integer of 1–2, or an optionally protected carboxyl group, and when n is 2–4, R¹ may independently have the above-mentioned substituent;

A is hydrogen atom, a halogen atom, a group represented by the formula —NR⁴R⁵, wherein in the formula, R⁴ and R⁵ are the same as or different from each other and each is hydrogen atom, an optionally substituted lower alkyl group, an acyl group, an optionally substituted arylalkyl group or an optionally substituted heteroarylalkyl group, or R⁴ and R⁵ may form a ring together with a nitrogen atom bonded thereto, which ring may further have a substituent, an optionally substituted aryl group, an optionally substituted heteroaryl group, an optionally substituted arylalkyl group or an optionally substituted heteroarylalkyl group;

X is a group represented by the formula —NR⁶—, wherein in the formula, R⁶ is hydrogen atom, an optionally substituted lower alkyl group, an optionally substituted arylalkyl group or an optionally substituted heteroarylalkyl group, or a group represented by the formula —N=;

Y is a group represented by —CO— or a group represented by the formula —C(B)=, wherein in the formula, B is hydrogen atom, a halogen atom, a formula represented by the formula —NR⁷R⁸, wherein in the formula, R⁷ and R⁸ may be the same as or different from each other and each is hydrogen atom, an optionally substituted lower alkyl group, an acyl group, an optionally substituted arylalkyl group or an optionally substituted heteroarylalkyl group, R⁷ and R⁸ may form a ring together with a nitrogen atom bonded thereto, which ring may further have a substituent, a group represented by the formula —O—R¹², wherein in the formula, R¹² is hydrogen atom, an optionally substituted lower alkyl group, an acyl group, an optionally substituted arylalkyl group or an optionally substituted heteroarylalkyl group, a group represented by the formula—S—R¹³, wherein in the formula, R¹³ is hydrogen atom, an optionally substituted lower alkyl group, an acyl group, an optionally substituted arylalkyl group or an optionally substituted heteroarylalkyl group, an optionally substituted aryl group, an optionally substituted heteroaryl group, an optionally substituted arylalkyl group or an optionally substituted heteroarylalkyl group; and the formula (VIII) means a double or single bond, provided that when the ring C is a benzene ring, the case where n is 0 is excluded.

From the above, the compound represented by the formula (VI) may be selected from the group consisting of:

4-(3-chloro-4-methoxybenzyl)amino-6-cyano-1-(4-hydroxypiperidino)phthalazine hydrochloride represented by the formula (IX)

4-(3-chloro-4-methoxyphenethyl)amino-6-cyano-1-(4-hydroxypiperidino)phthalazine hydrochloride represented by the formula (X)

4-[(3-chloro-4-methoxybenzyl)amino]-1-(2-hydroxy-7-azaspiro[3,5]non-7-yl)-6-phthalazine carbonitrile hydrochloride represented by the formula (XI)

1-(2-hydroxy-7-azaspiro[3,5]non-7-yl)-4-[(4-methoxy-3-methylbenzyl)amino]-6-phthalazine carbonitrile hydrochloride represented by the formula (XII)

(XII)

1-[4-fluoro-4-(hydroxymethyl)piperidino]-4-[(4-methoxy-3-methylbenzyl)amino]-6-phthalazine carbonitrile hydrochloride represented by the formula (XIII)

(XIII)

4-[(3-chloro-4-methoxyphenethyl)amino]-1-(2-hydroxy-7-azaspiro[3,5]non-7-yl)-6-phthalazine carbonitrile hydrochloride shown by the formula (XIV)

(XIV)

4-[(3-chloro-4-methoxybenzyl)amino]-1-(3-oxo-2-oxa-8-azaspiro[4,5]decen-8-yl)-6-phthalazine carbonitrile represented by the formula (XV)

(XV)

Still furthermore, the present invention is a method for the manufacture of an intraoral quickly disintegrating tablet where a slightly soluble pharmaceutical agent is dissolved in an organic solvent or an aqueous organic solvent together with a surfactant and/or a water-soluble polymer, then a saccharide is mixed with a molded product prepared by a coating of a filler or by a granulation together with a filler, an organic solvent, water or an aqueous organic solvent is added thereto and the mixture is kneaded and subjected to a compression-molding. Here, the term "molded product" means granules, fine granules, powder or the like and the molded product may be manufactured using, for example, a fluidized bed granulator, a tumbling granulator, an extrusion granulator or a spray-drying granulator.

Further, the present invention is a method for the manufacture of an intraoral quickly disintegrating tablet where a surfactant and/or a water-soluble polymer are/is added to a slightly soluble pharmaceutical agent followed by mixing, an organic solvent, water or an aqueous organic solvent is added thereto and the mixture is kneaded and subjected to a compression-molding.

The term "slightly soluble" means that the substance is slightly soluble in water, saliva, gastric juice, intestinal juice, etc., and that can be measured by common tests.

Here, the surfactant and/or the water-soluble polymer play(s) a role of improving the solubility whereby wetting of the slightly soluble pharmaceutical ingredient per se with water is improved. A method for improving the solubility of the pharmaceutical agent in accordance with the present invention is not only able to improve the solubility of the intraoral quickly disintegrating tablet containing the slightly soluble pharmaceutical agent and to ensure its quick disintegration in the mouth but also able to ensure the good touch on the tongue during the disintegration in the mouth.

During the course of the compression-molding in the present invention, it is preferred for keeping the good molding property of the tablet that the powder kneaded with an organic solvent, water or an aqueous organic solvent is filled in a mold and subjected to a compression-molding with a film.

Furthermore, the present invention is an intraoral quickly disintegrating tablet with an improved solubility containing a cyclic GMP phosphodiesterase inhibitor which is a slightly soluble pharmaceutical agent and also is a method for manufacturing the tablet.

Examples of the slightly soluble pharmaceutical agent in the present invention are nifedipine, phenytoin, nitrofurantoin, benoxaprofen, griseofulvin, sulfathiazole, tacrolimus, piroxicam, carbamazepine, phenacetin and cyclic GMP phosphodiesterase inhibitor although the present invention is not limited thereto.

Examples of the cyclic GMP phosphodiesterase inhibitor in the present invention are pyrazonopyrimidinone compounds (JP-B 9-50396) represented by 5-[2-ethoxy-5-(4-methyl-1-piperazinylsulfonyl)phenyl]-1-methyl-3-n-propyl-1,6-dihydro-7H-pyrazolo[4,3-d]pyrimidin-7-one (general name: sildenafil) of the formula (I); pyrazolopyrimidinone compounds represented by 1,3-dimethyl-6-(2-propoxy-5-methanesulfonamidophenyl)-1,5-dihydropyrazolo[3,4-d]pyrimidin-4-one of the formula (II) (JP-A 7-70128); (6R,12aR)-2,3,6,7,12,12a-hexahydro-2-methyl-6-(3,4-methylenedioxyphenyl)-pyrazino[2', 1':6, 1]-pyrido[3,4-b ]indol-1,4-dione) represented by the formula (IV) and (3S,6R,12aR)-2,3,6,7,12,12a-hexahydro-2,3-dimethyl-6-(3,4-methylenedioxyphenyl)-pyrazino[2', 1':6,1]pyrido[3,4-b ]-indol-1,4-dione represented by the formula (V) (WO 97/03675); 2-(4-carboxypiperidino)-4-(3,4-methylenedioxybenzyl)amino-6-chloroquinazoline represented by the formula (III) (WO 93/07124); a fused pyridazine compound represented by the formula (VI); and a pharmacologically acceptable salt thereof.

Examples of the compound shown by the formula (VI) are 4-(3-chloro-4-methoxybenzyl)amino-6-cyano-1-(4-hydroxypiperidino)phthalazine hydrochloride represented by the formula (IX) (JP-A 8-225541), 4-(3-chloro- 4-methoxyphenethyl)amino-6-cyano-1-(4-hydroxypiperidino) -phthalazine hydrochloride represented by the formula (X), 4-[(3-chloro-4-methoxybenzyl)amino]-1-(2-hydroxy-7-azaspiro[3,5]-non-7-yl)-6-phthalazine carbonitrile hydrochloride represented by the formula (XI), 1-(2-hydroxy-7-azaspiro[3,5]non-7-yl)-4-[(4-methoxy-3-methylbenzyl) amino]-6-phthalazine carbonitrile hydrochloride represented by the formula (XII), 1-[4-fluoro-4-(hydroxymethyl) piperidino]-4-[(4-methoxy-3-methylbenzyl) amino]-6-phthalazine carbonitrile hydrochloride shown by the formula (XIII), 4-[(3-chloro-4-methoxyphenethyl)amino]-1-(2-hydroxy-7-azaspiro[3,5]non-7-yl)-6-phthalazine carbonitrile hydrochloride represented by the formula (XIV) and 4-[(3-chloro-4-methoxybenzyl)amino]-1-(3-oxo-2-oxa-8-azaspiro[4,5]dece-8-yl)-6-phthalazine carbonitrile represented by the formula (XV).

However, the cyclic GMP phosphodiesterase inhibitor of the present invention is not limited to those compounds only.

Usually, the compounding ratio of the cyclic GMP phosphodiesterase inhibitor or the slightly soluble pharmaceutical agent in the present invention to 1 part by weight of the tablet is 0.0001–0.4 part by weight, preferably 0.005–0.3 part by weight or, more preferably, 0.01–0.25 part by weight.

An average particle diameter of the cyclic GMP phosphodiesterase inhibitor or the slightly soluble pharmaceutical agent per se is 1–100 $\mu$m, preferably 5–70 $\mu$m and more preferably, 5–50 $\mu$m.

With regard to the saccharide in the present invention, any saccharide may be used so far as it is soluble in water and is stable and its examples are mannitol, sucrose, lactose, trehalose, xylitol, erythritol, glucose, starch and dextrin. In the present invention, each of them may be used solely or two or more thereof may be used jointly.

The compounding ratio of the saccharide in the present invention varies depending upon the type of the cyclic GMP phosphodiesterase inhibitor or the slightly soluble pharmaceutical agent but, usually, it is 2–50 parts by weight, preferably 3–40 parts by weight or, more preferably, 4–30 parts by weight to 1 part by weight of the cyclic GMP phosphodiesterase inhibitor or the slightly soluble pharmaceutical agent.

An average particle size of the saccharide is 1–100 $\mu$m, preferably 5–70 $\mu$m or, more preferably, 5–50 $\mu$m.

The intraoral quickly disintegrating tablet of the present invention may be compounded with a binder if necessary.

Examples of the binder are polyvinylpyrrolidone, Macrogol, hydroxypropyl methylcellulose, methylcellulose, hydroxypropyl cellulose, hydroxypropyl methylcellulose phthalate, hydroxypropyl methylcellulose acetate succinate, carboxymethycellulose sodium, cellulose acetate phthalate, gum arabic, gelatin, methacrylic acid copolymer, carboxyvinyl polymer, polyvinyl alcohol, alpha-starch and pullulan. In the present invention, each of them may be used solely or two or more thereof may be used jointly and the use of polyvinylpyrrolidone is particularly preferred.

The compounding ratio of the binder in the present invention to 1 part by weight of the tablet is usually 0.001–0.1 part by weight or, preferably, 0.005–0.05 part by weight, and that may be appropriately increased or decreased so as to give desired disintegrating degree and hardness. Incidentally, the binder may be added in its powdery form to a mixture of the cyclic GMP phosphodiesterase inhibitor and the saccharide or may be added after dissolving in the organic solvent, pure water or the aqueous organic solvent.

The intraoral quickly disintegrating tablet according to the present invention is a tablet which is quickly disintegrated in the mouth after administration and is able to be easily taken even without water. In addition to the above-mentioned saccharide and binder, the intraoral quickly disintegrating tablet may be compounded with conventionally used filler, lubricant, disintegrating agent, sweetener and/or coloring agent if necessary.

The intraoral quickly disintegrating tablet may be prepared in such a manner that a saccharide and a binder are mixed with a cyclic GMP phosphodiesterase inhibitor, then conventionally used filler, lubricant, sweetener, coloring agent, disintegrating agent, etc. are added thereto if necessary, kneaded with an organic solvent, water or an aqueous organic solvent, filled in a mold and subjected to a compression-molding. The kneading and granulating operations carried out by adding such auxiliary agents for making the preparation and by adding such a solvent may be conducted using the conventionally used apparatus. For example, a fluidized bed granulator, a tumbling granulator, an extrusion granulator or a spray-drying drier may be used.

Examples of the filler are crystalline cellulose, ethylcellulose, dextrin, various kinds of cyclodextrin ($\alpha$-cyclodextrin, $\beta$-cyclodextrin and $\gamma$-cyclodextrin) as well as derivatives thereof and pullulan.

Examples of the lubricant are magnesium stearate, calcium stearate, stearic acid and talc; examples of the sweetener are aspartame, dipotassiumglycyrrhizinate, white sugar, licorice, saccharin and sodium saccharinate; and examples of the coloring agent are yellow iron sesquioxide, yellow iron oxide, Yellow #4 dye for food, Yellow #5 dye for food, (Yellow #4 dye for food aluminum lake), red iron oxide, iron sesquioxide, Red #2 dye for food, Red #3 dye for food and Red #102 dye for food. In the present invention, each of them may be used solely or two or more thereof may be used jointly.

Examples of the disintegrating agent are light silicic anhydride, crystalline cellulose, cross povidone, lowly substituted hydroxypropyl cellulose, cross carmellose sodium, calcium silicate, magnesium metasilicate aluminate, carboxymethyl cellulose, carboxymethyl cellulose calcium, hydroxypropyl starch, carboxymethyl starch sodium, partially $\alpha$-starch and sodium alginate. In the present invention, each of them may be used solely or two or more thereof may be used jointly.

In the present invention, an intraoral quickly disintegrating tablet may be manufactured in such a manner that a cyclic GMP phosphodiesterase inhibitor is mixed with a saccharide, a binder is further added thereto if necessary, the mixture is kneaded with an organic solvent, water or an aqueous organic solvent and the resulting wet powder is made into a form of a tablet followed by drying.

In the present invention, an intraoral quickly disintegrating tablet may be manufactured in such a manner that 1) a slightly soluble pharmaceutical agent is dissolved in an organic solvent together with a surfactant and/or a water-soluble polymer, coated on a filler or granulated together with a filler, a saccharide is mixed with the resulting granules, fine granules or powder or that 2) a slightly soluble pharmaceutical agent is mixed with a saccharide and a surfactant and/or a water-soluble polymer, then a binder, a disintegrating agent, a lubricant, a sweetener or a coloring agent is added thereto if necessary and the mixture is kneaded with an organic solvent, water or an aqueous organic solvent and, after that, any of the above-mentioned mixture is filled in a mold followed by subjecting to a compression molding.

Examples of the surfactant used here are sodium lauryl sulfate, sorbitan fatty acid ester, polyethylene glycol fatty acid ester, polyoxyethylene sorbitan fatty acid ester, polyoxyethylene alkyl ether, polyoxyethylene polyoxypropylene alkyl ether, polyoxyethylene polyoxypropylene block copolymer, polyoxyethylene alkyl phenyl ether, polyoxyethylene castor oil, polyoxyethylene hydrogenated castor oil, polyoxyethylene sorbitol fatty acid ester and polyoxyethylene glycerol fatty acid ester. In the present invention, each of them may be used solely or two or more thereof may be used jointly.

The compounding ratio of the surfactant in the present invention to 1 part by weight of the slightly soluble pharmaceutical agent is usually 0.0005–0.1 part by weight, preferably 0.001–0.08 parts by weight or, more preferably, 0.001–0.05 parts by weight.

Examples of the water-soluble polymer are hydroxypropyl methylcellulose, methylcellulose, hydroxypropyl cellulose, hydroxypropyl methylcellulose phthalate, hydroxypropyl methylcellulose acetate succinate, carboxymethyl cellulose sodium, celluloseacetatephthalate, gumarabic, agar, gelatin, sodium alginate, polyvinylpyrrolidone, aminoalkyl methacrylate copolymer, methacrylic acid copolymer, carboxyvinyl polymer, polyvinyl alcohol and Macrogol and, in the present invention, each of them may be used solely or two or more thereof may be used jointly.

The compounding ratio of the slightly soluble pharmaceutical agent to the water soluble polymer in the present invention is usually 0.001–0.6 parts by weight or, preferably, 0.005–0.1 part by weight of the water-soluble polymer to 1 part by weight of the slightly soluble pharmaceutical agent.

Further, the concentration of the water soluble polymer in the solution of the water soluble polymer is usually 0.1–40% by weight or, preferably, 1–20% by weight.

The solution of the water soluble polymer may be any of an aqueous solution, an organic solvent solution and an aqueous organic solvent solution containing the above-mentioned water soluble polymer.

The solvent which is used for the kneading stage in the manufacturing process for the intraoral quickly disintegrating tablet maybe any of an organic solvent, pure water and an aqueous organic solvent. Examples of the organic solvent or of that used for the aqueous organic solvent are ethanol, methanol, propanol and isopropanol and, preferably, ethanol. In the present invention, one of them may be used solely or two or more of them may be used jointly. The preferred compounding ratio of the organic solvent in the aqueous organic solvent is usually 0.05–0.99 parts by weight, more preferably 0.2–0.98 parts by weight or, further preferably, 0.25–0.98 parts by weight to 1 part by weight of the aqueous organic solvent.

In the molding of the wet powder, a lubricant may be applied, if necessary, on upper and lower sides of the kneaded mixture filled therein whereby an adhesion during the compressing step can be prevented but, for the manufacture in a more efficient and easier manner, it is preferred to use a tablet manufacturing apparatus which is disclosed in JP-A 8-19589. Thus, a wet powder is filled in a mold for the tablet molding of the tablet manufacturing apparatus and at least one surface of the wet powder in the mold is molded via an adhesion-preventing film whereby an adhesion of the wet powder to the metal mold for molding can be prevented and a quickly disintegrating tablets are able to be manufactured in an efficient manner.

The pressure applied upon the compression-molding of the wet powder after kneading the mixture or upon tableting via an adhesion-preventing film after filling in a mold in the present invention is usually 2–150 kg/cm$^2$, preferably 2–100 kg/cm$^2$ or, more preferably, 3–50 kg/cm$^2$.

The drying temperature after the compression-molding or the tableting in the present invention is usually 15–80° C., preferably 20–75° C. or, more preferably, 30–70° C.

The tablet hardness of the intraoral quickly disintegrating tablet prepared by the manufacturing method in accordance with the present invention is usually 1–15 kg/cm$^2$ preferably 1.5–10 kg/cm$^2$ or, more preferably, 2–6 kg/cm$^2$. Time for disintegration in the mouth of the intraoral quickly disintegrating tablet is usually 0.05–3 minute(s), preferably 0.05–1 minute or, more preferably, 0.1–0.5 minute.

The water content in the wet powder which is kneaded in the present invention is 0.01–25% by weight, preferably 0.1–20% by weight or, more preferably, 0.1–15% by weight of the kneaded mixture.

The intraoral quickly disintegrating tablet according to the present invention may, for example, be manufactured as follows. Thus, 75 g of sildenafil having the formula (I) which is a cyclic GMP phosphodiesterase inhibitor and 340.8 g of mannitol were well mixed in a mixer. To this mixture was added an aqueous ethanol solution where 4.2 g of polyvinylpyrrolidone K 30 were dissolved in 58.8 g of a 55% ethanol solution followed by kneading for about 3 minutes. After that, the kneaded mixture was subjected to a compression-molding using, for example, a tablet manufacturing apparatus disclosed in JP-A 8-19589 by filling in a mold via a film with a pestle having a diameter of 9.5 mm with a compressing pressure of 35 kg/cm$^2$. The molded product was dried in a drier of 50° C. for about 2 hours to manufacture intraoral quickly disintegrating tablets where each tablet (280 mg) contains 50 mg of sildenafil.

Alternatively, 1.5 g of 4-(3-chloro-4-methoxybenzyl) amino-6-cyano-1-(4-hydroxypiperazino) -phthalazine hydrochloride having the formula (IX) which is a slightly soluble cyclic GMP phosphodiesterase inhibitor and 0.015 g of sodium lauryl sulfate were dissolved in 100 g of a 70% ethanol solution heated at 70° C. After that, 40.08 g of mannitol were added thereto and the mixture was well mixed in a mixer, followed by drying to give a powder. To this powder is added an aqueous ethanol solution where 0.42 g of polyvinylpyrrolidone K30 is dissolved in 5.88 g of a 55% ethanol solution, and the mixture is kneaded for about 1 minute. Then the kneaded mixture is subjected to a compression-molding using a compression tester (Shimadzu Autograph) with a compressing pressure of 35 kg/cm² using a pestle having a diameter of 9.5 mm. The molded product is dried in a drier of 50° C. for about 2 hours to manufacture the tablets where each tablet (280 mg) contains 10 mg of the phthalazine compound having the formula (IX).

In accordance with the present invention, it is possible to manufacture an intraoral quickly disintegrating tablet which contains a cyclic GMP phosphodiesterase inhibitor having an improving effect for erectile dysfunction and has quick disintegrating property, solubility and appropriate strength in the mouth.

In accordance with the present invention, it is also possible to manufacture an intraoral quickly disintegrating tablet containing a slightly soluble pharmaceutical agent, being characterized in a quick dissolving in the mouth and having an appropriate strength.

Examples of the such effects will be shown as hereunder.

EXPERIMENTAL EXAMPLES

1) Good Physical Property of the Tablets Concerning the Present Invention

In a mixer, 1.5 g of a phthalazine compound having the formula (IX) {4-(3-chloro-4-methoxybenzyl)amino-6-cyano-1-(4-hydroxypiperidino) -phthalazine hydrochloride} and 40.08 g of mannitol were well mixed, an aqueous ethanol solution where 0.42 g of polyvinylpyrrolidone K 30 was dissolved in 5.88 g of a 55% ethanol solution was added and the mixture was kneaded for about 1 minute. The kneaded mixture was molded using a compression tester (Shimadzu Autograph) with a compressing pressure of 50 kg/cm² using a pestle having a diameter of 9.5 mm which was previously covered with a small amount of magnesium stearate. The molded product was dried in a drier of 60° C. for about 3 hours to manufacture the tablets where each tablet (280 mg) contained 10 mg of the phthalazine compound having the formula (IX).

When the physical property of the tablets was evaluated, the tablet hardness was 5.59 kg/cm² (mean value of five tablets) and the disintegrating time of the tablet was within 15 seconds and, therefore, it is apparent that the tablets have a good physical property as intraoral quickly disintegrating tablets.

Each one of the above tablets was subjected to an eluting test in each 900 ml of the first liquid (pH 1.2), the second liquid (pH 6.8) and pure water as regulated by the Disintegration Test Method of the Japanese Pharmacopoeia according to a puddle method (50 r.p.m.) of the Disintegration Test Method of the Japanese Pharmacopoeia using 10 mg of the phthalazine compound per se having the formula (IX) as a control. Incidentally, the eluted amount of the phthalazine compound having the formula (IX) was measured by means of a high-performance liquid chromatography using an ultraviolet absorptiometer (measured wave length=215 nm). Results of the eluting test are shown in FIGS. 1–3.

Figure 1:
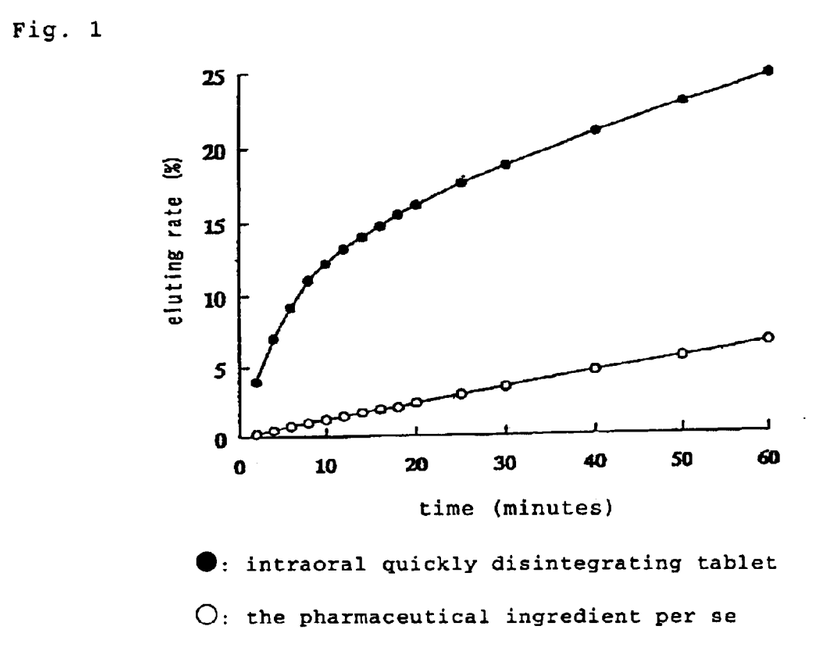
FIG. 1 is a graph showing the changes of the eluting rate in the first solution as regulated by the Japanese Pharmacopoeia concerning the phthalazine compound per se having the formula (IX) and the intraoral quickly disintegrating tablet containing the phthalazine compound.
Figure 2:
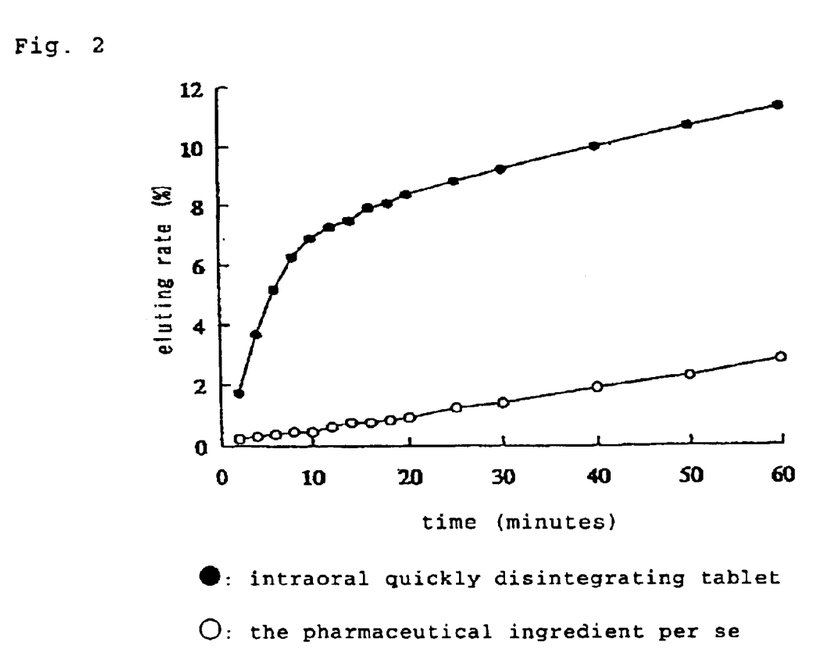
FIG. 2 is a graph showing the changes of the eluting rate in the second solution as regulated by the Japanese Pharmacopoeia concerning the phthalazine compound per se having the formula (IX) and the intraoral quickly disintegrating tablet containing the phthalazine compound.
Figure 3:
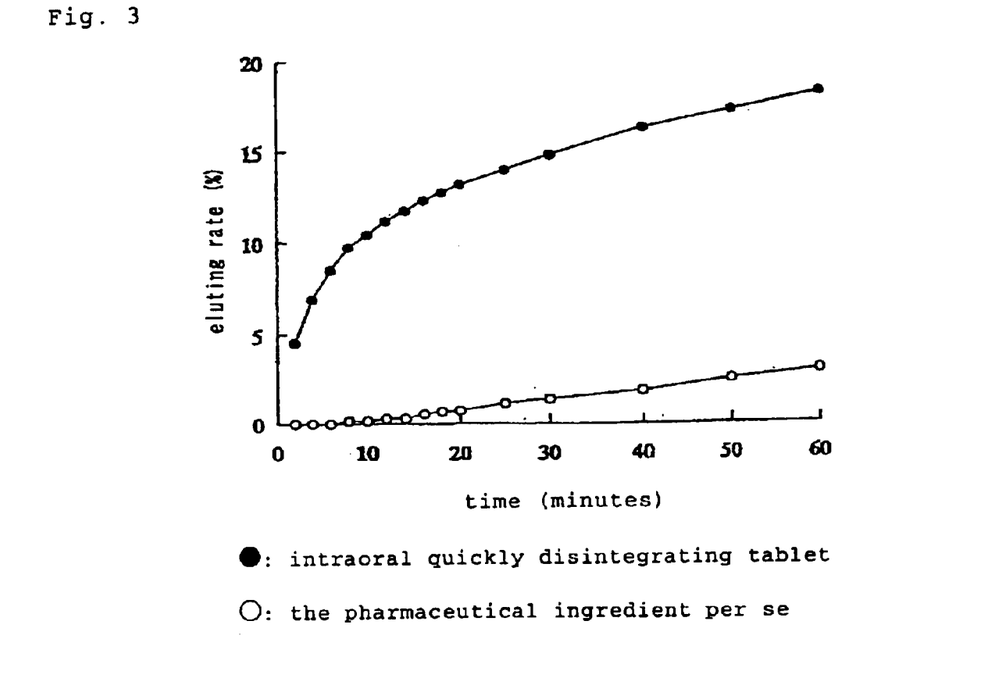
FIG. 3 is a graph showing the changes of the eluting rate in pure water concerning the phthalazine compound per se having the formula (IX) and the intraoral quickly disintegrating tablet containing the phthalazine compound.

From FIGS. 1–3, it is apparent that the intraoral quickly disintegrating tablet containing a cyclic GMP phosphodiesterase inhibitor according to the present invention shows quicker and better eluting characteristic as compared with the sole use of the agent per se.

2) Good Solubility of the Tablet According to the Present Invention Containing a Slightly Soluble Pharmaceutical Agent 4-(3-Chloro-4-methoxyphenethyl)amino-6-cyano-1-(4-hydroxypiperidino)phthalazine hydrochloride having the formula (X) has a very slight solubility and its absorption in vivo is worried about.

Therefore, a pharmaceutical preparation where the solubility of the phthalazine compound having the formula (X) was improved was manufactured.

Thus, 16 g of the phthalazine compound having the formula (X) and 1.6 g of sodium lauryl sulfate were dissolved in 1000 g of a 55% ethanol solution heated at 60° C. (step A). Separately, a mixture of 198.4 g of mannitol and 8 g of light silicic anhydride was subjected to a disintegration mixing using a sample mill (step B). Then the mixed powder obtained in the step B was subjected to a fluidized bed granulation using the solution obtained in the step A to prepare granules, fine granules or powder. Incidentally, temperatures of the sucking and exhausting air during the fluidized bed granulation were set at 70° C. and 50° C., respectively.

After that, 21 g of the granules, fine granules or powder containing the phthalazine compound having the formula (X) were/was well mixed with 20.6 g of mannitol in a mixer, an aqueous ethanol solution where 0.42 g of polyvinylpyrrolidone K 30 was dissolved in 5.88 g of a 25% ethanol solution was added and the mixture was kneaded for about 1 minute. The kneaded mixture was molded using a compression tester (Shimadzu Autograph) with a compressing pressure of 28.5 kg/cm² using a pestle having a diameter of 9.5 mm which was previously covered with a small amount of magnesium stearate.

The molded product was dried in a drier of 60° C. for about 3 hours to manufacture the tablets where each tablet (280 mg) contained 10 mg of the phthalazine compound having the formula (X).

When the physical property of the tablets was evaluated, the tablet hardness was 5.53 kg/cm² (mean value of six tablets) and the disintegrating time of the tablet was 18.2 seconds (mean value of six tablets) and, therefore, it is apparent that the tablets have a good physical property as intraoral quickly disintegrating tablets.

One of the above tablets was subjected to an eluting test in 900 ml of the first solution (pH 1.2) as regulated by the Disintegration Test Method of the Japanese Pharmacopoeia using a tablet containing 10 mg of the phthalazine compound per se having the formula (X) as a control and the eluting rate was evaluated using an ultraviolet absorptiometer (measured wave length=240 nm). Result of the eluting test is shown in FIG. 4.

Incidentally, the preparation which was prepared by the conventional manufacturing method and used as a control was prepared according to the following method.

Thus, 10 g of the phthalazine compound having the formula (X), 85.3 g of lactose and 20 g of corn starch were mixed and subjected to a granulation by a tumbling granulator together with a gradual addition of a 7% aqueous solution of polyvinylpyrrolidone K 30 where 7 g of polyvinylpyrrolidone K 30 were dissolved whereupon a granulated product was obtained. This granulated product was dried at 60° C. for 20 hours and sieved through a sieve of 24 mesh where 122 g of a sieved product was obtained, 7 g of cross carmellose sodium and 0.7 g of magnesium stearate were added thereto and the mixture was made into tablets using a pelletizer by a pestle having a diameter of 7 mm with a compressing pressure of 600 kg/cm$^2$ to manufacture the conventional tablets where each tablet (130 mg) contained 10 mg of the phthalazine compound having the formula (X).

Figure 4:
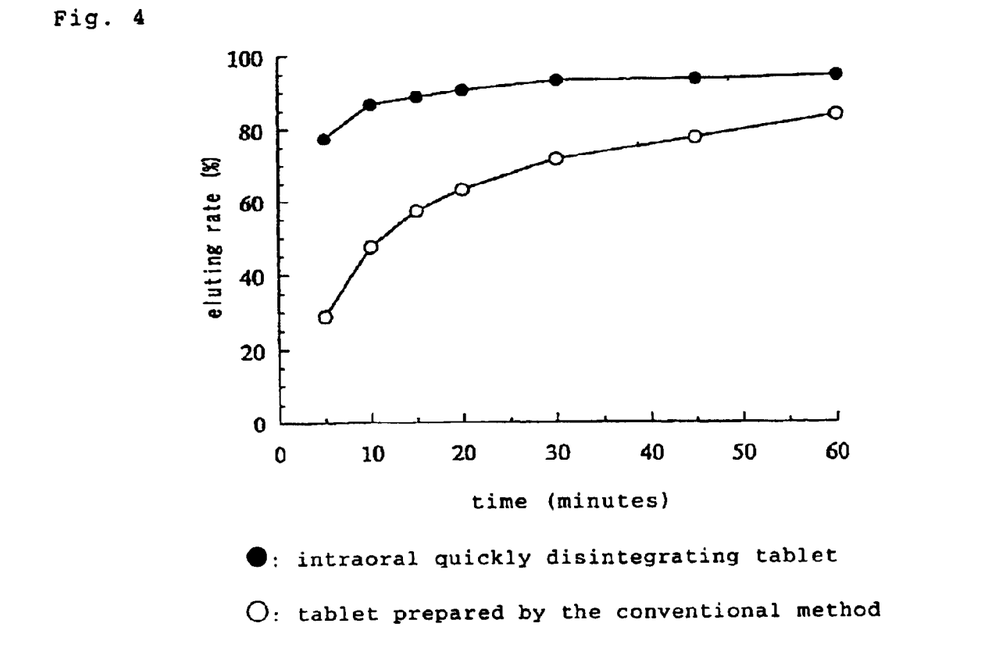
FIG. 4 is a graph showing the changes of the eluting rate in pure water concerning the intraoral quickly disintegrating tablet containing the phthalazine compound having the formula (X) and the tablet which is prepared by the conventional manufacturing method.

As shown in FIG. 4, the intraoral quickly disintegrating tablet containing the phthalazine compound having the formula (X) showed a significantly quicker eluting characteristic as compared with the preparation which was prepared by the conventional manufacturing method. In general, preparations having a good solubility show little dispersion in an absorbing property and, in addition, a higher bioavailability is often achieved. It is apparent that the intraoral quickly disintegrating tablet in accordance with the present invention shows a better solubility than the preparation which was prepared by the conventional manufacturing methods.

EXAMPLES

The present invention will now be further illustrated by way of the following Examples although the present invention is not limited thereto.

Example 1

In a mixer, 50 g of sildenafil which is a cyclic GMP phosphodiesterase inhibitor having a formula (III) and 228 g of mannitol were well mixed. To this mixture was added an aqueous ethanol solution where 2 g of polyvinylpyrrolidone K 30 was dissolved in 15 g of a 5% ethanol solution, followed by kneading for about 3 minutes. The resulting kneaded wet powder was subjected to a compression-molding by a method mentioned in JP-A 8-19589 (the kneaded mixture was filled in a mold for the tablet molding of the pelletizer and at least one surface of the wet powder in the above-mentioned mold was molded into a tablet by a metal mold for the molding via an adhesion preventing film), to manufacture tablets where each tablet contained 50 mg of sildenafil.

Hardness of the tablet was about 5 kg/cm$^2$ and the disintegrating time thereof in pure water was within 15 seconds.

Example 2

To 280 g of the kneaded mixture obtained in Example 1 were added 1.4 g of a lowly-substituted hydroxypropyl cellulose and 0.1 g of magnesium stearate, followed by mixing. The mixture was subjected to tableting by the same method as in Example 1, to give tablets where each tablet contained 50 mg of sildenafil.

Example 3

In a mixer, 10 g of a phthalazine compound having the formula (IX) {4-(3-chloro-4-methoxybenzyl)-amino-6-cyano-1-(4-hydroxypiperidino)phthalazine hydrochloride}, 267 g of mannitol and 3 g of polyvinylpyrrolidone K 30 were well mixed. To this mixture were added 40 g of 25% ethanol, followed by kneading for about 1 minute. The resulting kneaded mixture was subjected to the same operation as in Example 1 via an adhesion preventing film, to manufacture tablets where each tablet contained 10 mg of the phthalazine compound having the formula (IX).

Example 4

Into 6000 g of a 25% ethanol solution heated at 50° C. were dissolved 100 g of the phthalazine compound having the formula (X) and 15 g of polyoxyethylene hydrogenated castor oil (step A). Separately, a mixture of 1240 g of mannitol and 100 g of light silicic anhydride was disintegrated and mixed using a hammer mill (step B). Next, the mixed powder obtained in the step B was subjected to a tumbling granulation using a solution prepared in the step A to prepare granules, fine granules or powder. In a mixer, 147 g of the granules, the fine granules or the powder prepared as such and 130 g of mannitol were well mixed, a 55% ethanol solution where 3 g of hydroxypropyl methylcellulose were dissolved therein was added and the mixture was kneaded for about 3 minutes. The kneaded mixture was molded by a means mentioned in JP-A 8-19589 (the kneaded mixture was filled in a mold for the tablet molding of the pelletizer and at least one surface of the wet powder in the above-mentioned mold was molded into a tablet by a metal mold for the molding via an adhesion preventing film) using a pestle having a diameter of 9.5 mm and with a compressing pressure of 45 kg/cm$^2$.

What is claimed is:

1. An intraoral quickly disintegrating tablet comprising a cyclic GMP phosphodiesterase inhibitor and a saccharide selected from the group consisting of mannitol, xylitol, and erythritol, wherein the saccharide is present in a ratio of 4 to 30 parts by weight to 1 part by weight of the cyclic GMP phosphodiesterase inhibitor.

2. The tablet as claimed in claim 1, which further comprises a binder.

3. A method for manufacturing the tablet defined in claim 1, which comprises mixing a cyclic GMP phosphodiesterase inhibitor with a saccharide, kneading the mixture with an organic solvent, water or an aqueous organic solvent and subjecting it to a compression-molding.

4. The method as claimed in claim 3, which comprises filling the kneaded mixture in a mold and subjecting it to a compression-molding with a film.

5. The tablet as claimed in any one of claims 1 or 2, wherein the cyclic GMP phosphodiesterase inhibitor is selected from the group consisting of:

5-[2-ethoxy-5-(4-methyl-1-piperazinylsulfonyl)phenyl]-1-methyl-3-n-propyl-1,6-dihydro-7H-pyrazolo[4,3-d]pyrimidin-7-one represented the formula (I)

1,3-dimethyl-6-(2-propoxy-5-methanesulfonamidophenyl)-1,5-dihydropyrazolo[3,4-d]pyrimidin-4-one represented by the formula (II)

2-(4-carboxypiperidino)-4-(3,4-methylenedioxybenzyl)amino-6-chloroquinazoline represented by the formula (III)

(6R,12aR)-2,3,6,7,12,12a-hexahydro-2-methyl-6-(3,4-methylenedioxyphenyl)-pyrazino[2', 1':6,1]pyrido[3,4-b]-indol-1,4-dione represented by the formula (IV)

(3S,6R,12aR)-2,3,6,7,12,12a-hexahydro-2,3-dimethyl-6-(3,4-methylenedioxyphenyl)-pyrazino[2', 1':6,1]pyrido[3,4-b]-indol-1,4-dione shown by the formula (V)

or a pharmacologically acceptable salt thereof.

6. The tablet as claimed in any one of claims 1 or 2, wherein the cyclic GMP phosphodiesterase inhibitor is a compound selected from the group consisting of:

4-(3-chloro-4-methoxybenzyl)amino-6-cyano-1-(4-hydroxypiperidino)phthalazine hydrochloride represented by the formula (IX)

4-(3-chloro-4-methoxyphenethyl)amino-6-cyano-1-(4-hydroxypiperidino)phthalazine hydrochloride represented by the formula (X)

4-[(3-chloro-4-methoxybenzyl)amino]-1-(2-hydroxy-7-azaspiro[3,5]non-7-yl)-6-phthalazine carbonitrile hydrochloride represented by the formula (XI)

1-(2-hydroxy-7-azaspiro[3,5]non-7-yl)-4-[(4-methoxy-3-methylbenzyl)amino]-6-phthalazine carbonitrile hydrochloride represented by the formula (XII)

(XII)

1-[4-fluoro-4-(hydroxymethyl)piperidino]-4-[(4-methoxy-3-methylbenzyl)amino]-6-phthalazine carbonitrile hydrochloride represented by the formula (XIII)

(XIII)

4-[(3-chloro-4-methoxyphenethyl)amino]-1-(2-hydroxy-7-azaspiro[3,5]non-7-yl)-6-phthalazine carbonitrile hydrochloride shown by the formula (XIV)

(XIV)

4-[(3-chloro-4-methoxybenzyl)amino]-1-(3-oxo-2-oxa-8-azaspiro[4,5]decen-8-yl)-6-phthalazine carbonitrile represented by the formula (XV).

(XV)

7. The method for manufacturing as claimed in any one of claims 3 or 4, wherein the cyclic GMP phosphodiesterase inhibitor is selected from the group consisting of:
5-[2-ethoxy-5-(4-methyl-1-piperazinylsulfonyl)phenyl]-1-methyl-3-n-propyl-1,6-dihydro-7H-pyrazolo[4,3-d]pyrimidin-7-one represented by the formula (I), and
a compound represented by the formula (VI),
or pharmacologically acceptable salts thereof.

* * * * *